US011162925B2

(12) United States Patent
Cardin

(10) Patent No.: US 11,162,925 B2
(45) Date of Patent: Nov. 2, 2021

(54) HIGH PERFORMANCE SUB-AMBIENT TEMPERATURE MULTI-CAPILLARY COLUMN PRECONCENTRATION SYSTEM FOR VOLATILE CHEMICAL ANALYSIS BY GAS CHROMATOGRAPHY

(71) Applicant: Entech Instruments Inc., Simi Valley, CA (US)

(72) Inventor: Daniel B. Cardin, Simi Valley, CA (US)

(73) Assignee: Entech Instruments Inc., Simi Valley, CA (US)

( * ) Notice: Subject to any disclaimer, the term of this patent is extended or adjusted under 35 U.S.C. 154(b) by 202 days.

(21) Appl. No.: 16/175,230

(22) Filed: Oct. 30, 2018

(65) Prior Publication Data

US 2019/0137458 A1  May 9, 2019

Related U.S. Application Data

(60) Provisional application No. 62/581,459, filed on Nov. 3, 2017.

(51) Int. Cl.
   *G01N 30/72* (2006.01)
   *G01N 33/00* (2006.01)
   (Continued)

(52) U.S. Cl.
   CPC ....... *G01N 30/7206* (2013.01); *G01N 30/467* (2013.01); *G01N 30/6043* (2013.01);
   (Continued)

(58) Field of Classification Search
   CPC ............ G01N 30/7206; G01N 30/467; G01N 30/6043; G01N 30/6078; G01N 33/0014;
   (Continued)

(56) References Cited

U.S. PATENT DOCUMENTS 4,180,389 A  12/1979  Paul
5,014,541 A  5/1991  Sides et al.
(Continued)

FOREIGN PATENT DOCUMENTS

CN       1346055 A    4/2002
CN     102393429 A    3/2012
(Continued)

OTHER PUBLICATIONS

Miller,Benjamin Medusa: A Sample Preconcentration and GC/MS Detector System for in Situ Measurements of Atmospheric Trace Halocarbons, Hydrocarbons, and Sulfur Compounds Anal. Chem. 2008, 80, 1536-1545, Scripps Institution of Oceanography, University of California Mar. 5, 2009 (Year: 2009).*

(Continued)

*Primary Examiner* — Herbert K Roberts
*Assistant Examiner* — Monica S Young
(74) *Attorney, Agent, or Firm* — Kubota & Basol LLP

(57) ABSTRACT

The disclosed system and method improve analysis of chemical samples for measurement of trace volatile chemicals, such as by Gas Chromatography (GC) and Gas Chromatography/Mass Spectrometry (GCMS). The system can include two traps in series, the first of which removes most of the unwanted water vapor, while the second trap preconcentrates the sample using a series of capillary columns of increasing adsorption strength. The sample can be backflushed from the second trap directly to a chemical analyzer without splitting which can maximize sensitivity. The system improves elimination of water vapor and fixed gases from the sample prior to analysis, resulting in detection limits as low as 0.001 PPBb. The second trap allows faster release of the sample upon injection to the chemical analyzer without additional focusing, and can be cleaned up
(Continued)

faster when exposed to high concentration samples relative to packed traps.

16 Claims, 2 Drawing Sheets

(51) Int. Cl.
  *G01N 30/46* (2006.01)
  *G01N 30/60* (2006.01)
  *G01N 1/40* (2006.01)
  *G01N 30/02* (2006.01)
  *G01N 30/12* (2006.01)
  *G01N 30/40* (2006.01)

(52) U.S. Cl.
  CPC ..... *G01N 30/6078* (2013.01); *G01N 33/0014* (2013.01); *G01N 1/405* (2013.01); *G01N 30/40* (2013.01); *G01N 30/461* (2013.01); *G01N 30/72* (2013.01); *G01N 2001/4033* (2013.01); *G01N 2030/025* (2013.01); *G01N 2030/121* (2013.01); *G01N 2030/7226* (2013.01); *G01N 2033/0019* (2013.01)

(58) Field of Classification Search
  CPC ...... G01N 1/405; G01N 30/40; G01N 30/461; G01N 30/72; G01N 2001/4033; G01N 2030/025; G01N 2030/121; G01N 2030/7226; G01N 2033/0019
  USPC .......................................................... 73/23.41
  See application file for complete search history.

(56) References Cited

U.S. PATENT DOCUMENTS

| | | | |
|---|---|---|---|
| 5,135,549 A | 8/1992 | Phillips et al. | |
| 5,141,534 A * | 8/1992 | Sacks | G01N 30/12 96/102 |
| 5,191,211 A * | 3/1993 | Gorman, Jr. | G01N 30/06 250/282 |
| 5,288,310 A * | 2/1994 | Peters | G01N 30/12 96/104 |
| 5,392,634 A * | 2/1995 | Asano | G01N 30/40 422/89 |
| 5,402,668 A * | 4/1995 | Murakami | G01N 33/0016 436/161 |
| 5,449,902 A * | 9/1995 | Onishi | G01N 30/728 250/281 |
| 5,492,555 A * | 2/1996 | Strunk | G01N 30/463 73/23.37 |
| 5,547,497 A * | 8/1996 | Klemp | G01N 30/12 73/23.41 |
| 5,596,876 A | 1/1997 | Manura et al. | |
| 5,720,798 A | 2/1998 | Nickerson et al. | |
| 5,929,321 A | 7/1999 | Bertrand | |
| 6,086,767 A * | 7/2000 | Walters | B01D 11/0203 210/198.2 |
| 6,614,228 B2 | 9/2003 | Hofmann et al. | |
| 6,632,268 B2 | 10/2003 | Seeley | |
| 6,989,129 B2 | 1/2006 | Licklider et al. | |
| 7,451,634 B2 | 11/2008 | Gamache et al. | |
| 7,642,089 B2 | 1/2010 | Pieper et al. | |
| 7,647,812 B2 * | 1/2010 | Arnold | G01N 30/468 73/23.39 |
| 7,823,439 B2 * | 11/2010 | Fisher | G01N 30/465 73/23.42 |
| 8,075,842 B1 * | 12/2011 | Meece | G01N 1/4055 422/83 |
| 8,143,071 B2 | 3/2012 | Gjerde | |
| 8,613,215 B2 * | 12/2013 | Lambertus | G01N 30/465 73/23.42 |
| 8,621,912 B2 * | 1/2014 | Guieze | G01N 30/6095 73/23.42 |
| 9,188,568 B2 | 11/2015 | Ebeler et al. | |
| 9,228,984 B2 * | 1/2016 | Lu | G01N 30/461 |
| 9,240,311 B2 | 1/2016 | Whitehouse et al. | |
| 9,627,188 B2 | 4/2017 | Ariya et al. | |
| 2001/0027722 A1 * | 10/2001 | Bremer | G01N 30/12 95/82 |
| 2003/0109794 A1 | 6/2003 | Phillips | |
| 2005/0014156 A1 | 1/2005 | Pawliszyn | |
| 2005/0124076 A1 | 6/2005 | Tseng et al. | |
| 2006/0191414 A1 * | 8/2006 | Lange | G01N 30/12 96/101 |
| 2006/0245975 A1 | 11/2006 | Tipler et al. | |
| 2007/0071638 A1 | 3/2007 | Kraiczek et al. | |
| 2008/0264491 A1 | 10/2008 | Klee et al. | |
| 2008/0289397 A1 | 11/2008 | Hassan et al. | |
| 2009/0238722 A1 | 9/2009 | Mora-Fillat et al. | |
| 2010/0022764 A1 | 1/2010 | Otoshi et al. | |
| 2010/0242579 A1 | 9/2010 | Tipler et al. | |
| 2014/0299547 A1 | 10/2014 | Muller-Spath et al. | |
| 2015/0233876 A1 | 8/2015 | Dellea et al. | |
| 2016/0332141 A1 | 11/2016 | Machida et al. | |
| 2017/0284978 A1 | 10/2017 | Cardin | |
| 2019/0118171 A1 | 4/2019 | Cardin | |

FOREIGN PATENT DOCUMENTS

| | | |
|---|---|---|
| CN | 102302886 B | 8/2013 |
| CN | 103499662 A | 1/2014 |
| CN | 104792604 A | 7/2015 |
| CN | 204630990 U | 9/2015 |
| CN | 108387668 A | 8/2018 |
| EP | 0 597 602 A1 | 5/1994 |
| EP | 0806661 A1 | 11/1997 |
| EP | 2757369 A1 | 7/2014 |
| JP | 6-194351 A | 7/1994 |
| JP | 7-253421 A | 10/1995 |
| JP | H-11248694 A | 9/1999 |
| JP | 11-304784 A | 11/1999 |
| JP | 2003-262625 A | 9/2003 |
| JP | 2005-283317 A | 10/2005 |
| JP | 2009-2711 A | 1/2009 |
| JP | 2009-236539 A | 10/2009 |
| JP | 2014-529080 A | 10/2014 |
| JP | 2016-109298 A | 6/2016 |
| JP | 2017-173281 A | 9/2017 |
| WO | 2011/099079 A1 | 8/2011 |
| WO | WO-2017/176794 | 10/2017 |

OTHER PUBLICATIONS

HayeSep D specification sheet (Year: 2020).*
International Search Report dated Feb. 12, 2019, for PCT Patent Application No. PCT/US2018/057151, filed Oct. 23, 2018, five pages.
International Search Report dated Feb. 12, 2019, for PCT Patent Application No. PCT/US2018/058349, filed Oct. 31, 2018, five pages.
Non-Final Office Action dated Dec. 17, 2018, for U.S. Appl. No. 15/479,122, filed Apr. 4, 2017, 13 pages.
Examiner's Answer to Appeal Brief received for U.S. Appl. No. 15/479,122, dated Apr. 7, 2020, 22 pages.
Final Office Action dated Apr. 23, 2018, for U.S. Appl. No. 15/479,122, filed Apr. 4, 2017, 14 pages.
GL Science. (Date Unknown). "Multipurpose Sampling Thermal Desorption System MSTD258," GL Science, located at: URL: https://www.glsciences.com/c-product/sample/sa-instruments/multipurpose-sampling-thermal-desorption-system-mstd258/, 4 pages.
International Search Report dated Jul. 4, 2017, for PCT Patent Application No. PCT/US2017/025993, filed Apr. 4, 2017, six pages.
Materic, D. et al. (Dec. 2015). "Methods in Plant Foliar Volatile Organic Compounds Research," ResearchGate 2018, 25 pages.
Mclaughlin, L. G., et al. (Nov. 28, 1989). "Determination of dexamethasone in bovine tissues by coupled-column normal-phase high-performance liquid chromatography and capillary gas chromatography—mass spectrometry," Drug Testing and Toxicology, NYS College of Veterinary Medicine, Cornell University, 925

(56) References Cited

OTHER PUBLICATIONS

Warren Drive, Ithaca, NY 14850 U.S.A. located at: http://www.sciencedirect.com/science/article/pii/S0378434700838037?via%3Dihub, 19 pages.

Non-Final Office Action dated Dec. 4, 2017, for U.S. Appl. No. 15/479,122, filed Apr. 4, 2017, 12 pages.

Packham, A. J. et al. (Oct. 1989). "Complex Sample Analysis by Cybernetic Multi-dimensional Chromatography," Analytical Proceedings, vol. 26, Department of Instrumentation and Analytical Science, UMIST, Manchester, M60 1QD, located at: http://pubs.rsc.org/-/content/articlelanding/1989/ap/ap9892600336#!divAbstract, 17 pages.

Notice of Allowance received for U.S. Appl. No. 15/479,122, dated Mar. 24, 2021, 7 pages.

Patent Board Decision received for U.S. Appl. No. 15/479,122, dated Mar. 19, 2021, 7 pages.

Search Report received for Chinese Patent Application No. 201780029443.5, dated Jan. 26, 2021, 5 pages (2 page of English Translation and 3 page of Official Copy).

Supplemental Notice of Allowance received for U.S. Appl. No. 15/479,122, dated Apr. 1, 2021, 2 pages.

\* cited by examiner

HIGH PERFORMANCE SUB-AMBIENT TEMPERATURE MULTI-CAPILLARY COLUMN PRECONCENTRATION SYSTEM FOR VOLATILE CHEMICAL ANALYSIS BY GAS CHROMATOGRAPHY

CROSS-REFERENCE TO RELATED APPLICATIONS

This application claims the benefit of U.S. Provisional Patent Application No. 62/581,459, filed on Nov. 3, 2017, the entire disclosure of which is incorporated herein by reference in its entirety for all purposes.

FIELD OF THE DISCLOSURE

This relates to sample preconcentration and more particularly to a system and method for sample preconcentration that removes water from the sample prior to trapping at cold temperatures with a multi-capillary column trapping system (MCCTS).

BACKGROUND OF THE DISCLOSURE

Gas Chromatography (GC) typically provides analysis of gas phase chemicals with quantitative analysis limited to target compounds occurring in concentrations of at least 20 PPBv in a sample unless the chemicals within the sample are pre-concentrated prior to GC injection. Many applications require analysis of chemicals with concentrations as low as 0.001 PPB in order to reach olfactory detection limits when analyzing for aroma, fragrance, or odor containing compounds. Also, many chemicals in air are found to create a health risk at levels as low as 0.002 to 0.02 PPB, and the monitoring of these compounds is becoming more important to ensure a healthy environment both indoors and outdoors. Finally, many polar and non-polar VOCs are known to have an effect on ozone generation in urban atmospheres, so their monitoring is required to create strategies to try to reduce the concentrations of ozone in regulatory non-attainment areas.

One of the most successful systems for analyzing both polar and non-polar VOCs ranging from C2 Hydrocarbons boiling at about −90 deg C., to Naphthalene and C12 Hydrocarbons boiling at about +230 deg C. is a two trap preconcentration system using a cold, empty trap to eliminate most of the water vapor from the sample, followed by trapping on a packed adsorbent trap cooled to −10 to −60 deg C. The first trap can remove up to 98% of the water vapor in the gas sample, which is important as excess water affects the performance of the capillary GC column while also suppressing the response of the mass spectrometer and other detectors. All other compounds pass through this first dehydration stage either because of their very low boiling points (air, CO2, methane, etc), or because the chemicals at low to sub-PPB levels are still well below their saturation point at −10 C to −60 C and therefore remain in the gas phase. After passing through the first dehydration trap, compounds pass into the second stage which traps all compounds of interest, but allows the fixed gases to pass through with very little retention (Nitrogen, Oxygen, Argon, Methane, and Carbon Dioxide). The most common packed trap adsorbent has been Tenax TA, but other adsorbents have also been used.

This combination of cold trap dehydration and cold adsorbent trapping works well in many cases, but has some drawbacks. First, the cold packed trap releases the adsorbed sample too slowly to allow rapid injection into a high performance capillary GC, so a 3rd "focusing" stage is usually required to reduce the volume further to allow very fast injection rates into a capillary GC. Peak broadening occurs when injection rates are not fast enough, causing a loss of GC resolution and a reduction in analyzer sensitivity. Using a final 3rd stage focusing trap uses liquid nitrogen if the $3^{rd}$ stage is an uncoated tube, which requires temperatures below about −150° C. to collect the full range of compounds of interest. Cold packed micro traps have also been used to "focus" the sample at temperatures from −20° C. to −60° C., but this can result in increased system contamination by adding another adsorbent trap, while also increasing the complexity of the system, and therefore its potential reliability. Focusing the sample after trapping requires additional time which slows down sample throughput rates, adversely affecting laboratory productivity.

A second problem arises from the use of packed adsorbent traps in general. These traps are packed with adsorbent particles ranging in size from 20 to 100 mesh in order to allow enough volume between the particles so that the resistance to gas flow is not too great. That is, the use of particles smaller than 100 mesh in a packed adsorbent trap can restrict the flow so much that it will require too much time or to too high a pressure drop across the trap to get a reasonable flow rate. However, particles in the range of 20-100 mesh are large enough that if they are exposed to samples containing higher concentrations, it can take a while to completely out-gas residual carryover. In general, the required bake out times even when low concentration gases are preconcentrated are relatively long, again impacting analyzer productivity.

A third problem with packed traps comes when trying to eliminate all of the Carbon Dioxide (CO2) and residual molecular Nitrogen from the sample without loss of the light C2 Hydrocarbons; namely Ethane, Ethylene, and Acetylene. These compounds are often monitored down to sub-part-per-billion levels, in the presence of Carbon Dioxide that is at 500,000 to 1 million part per billion (500-1000 PPM) in the atmosphere or in indoor air. When using packed traps that require the use of larger adsorbent particles sizes within the trap, it can be difficult to purge out all of the CO2 and residual N2 without causing the C2 Hydrocarbons to break through the trap due to their high volatility. Simply due to the shear amount of CO2 (often 1-10 million times the concentration of C2 Hydrocarbons) and N2 (780 million PPB in air) and the difficulty in purging all of the CO2 and N2 out of the large adsorbent particles, a substantial amount of CO2 and N2 remains and is co-injected into the GC or GCMS, causing problems with both chromatography and mass spectrometry detection, as Ethylene and N2 both have a molecular weight of 28 amu, and CO2 breaks down in a mass spectrometer to also yield a significant mass 28 amu ion ($CO^+$), so both residual N2 and CO2 can interfere with low level Ethylene measurements, which can create background interferences. Excess CO2 can also poison Al2O3 PLOT columns, which are one of the more popular columns for separating C2 Hydrocarbons, so relatively complete elimination is essential.

A final issue also related to the use of packed traps is caused by a phenomenon called "channeling". When adsorbents heat up they expand as do most solids, and when they cool down they contract. Upon cool down, channels or gaps are created within the adsorbent that can cause gas flow to prefer these lower impedance flow paths during trapping, causing chemicals to penetrate further into the trap than desired. The further into the trap the sample reaches, the lower the recovery during analysis, especially for less volatile compounds. Since these channels tend to form differently from one cooling and trapping event to the next, the extent of penetration into the trap changes, affecting recovery and analytical system consistency.

SUMMARY OF THE DISCLOSURE

This relates to sample preconcentration and more particularly to a system and method for sample preconcentration that removes water from the sample prior to trapping at cold temperatures with a multi-capillary column trapping system (MCCTS). The disclosed approach preconcentrates gas phase samples containing volatile chemicals with boiling points from −100° C. to >230° C. to reduce their volume prior to injection into a Gas Chromatograph (GC). Two separate traps can be used: an inert cold trap to condense out most of the moisture (e.g., water vapor) in the sample, and a second capillary trap (e.g., a multi capillary column trapping system (MCCTS)) consisting of multiple stages that are optionally cooled down to sub-ambient levels to further increase the retention of compounds boiling as low as −100 deg C. including C2 hydrocarbons, Hydrogen Sulfide, and Formaldehyde. The dehydration trap removes enough moisture to reduce or eliminate interferences when performing high performance capillary gas chromatography while also reducing or eliminating interferences in GC detectors, such as mass spectrometers. The MCCTS consists of several short (e.g., a few inches to a few meters in length) GC capillary columns of increasing strength that are connected in series to increase or maximize the boiling point range of compounds recovered. In some embodiments, cooling of these capillary columns allows all compounds to trap within a small enough volume that secondary focusing is not required prior to split-less injection into a gas chromatograph. The very small sorbent particle size used in the stronger sections of the capillary trap optionally allow much faster and more complete release of compounds collected as compared to previous packed trap technology, resulting in higher resolution chromatography and far less carryover. These very small particles can also allow much faster diffusive elimination of fixed gases such as N2, Methane, and CO2, which can allow their concentrations to drop down to sub-PPB levels hundreds of times faster than when using larger particles in packed traps, providing far less background and interference on the GC column and in a mass spectrometer detector.

The disclosed system and method can be used for dozens of applications, including the analysis of C2-C12 Hydrocarbons. Halogenated VOCs, Polar VOCs containing Oxygen. Nitrogen. and Sulfur, and many other volatile. GC compatible chemicals all at concentrations from 0.001 PPB to 1000 PPM. In particular, compounds such as Formaldehyde and H2S that have poor recovery using other techniques are shown to recover much better using the disclosed system. Air or other gas samples can be introduced directly into the trapping system, or samples can be collected first in vacuum canisters or Tedlar bags for transfer to a laboratory for analysis. No other solution allows the GCMS analysis of such a complete range of volatile chemicals in indoor or outdoor air while quickly eliminating any system background after exposure to higher concentration samples.

DETAILED DESCRIPTION

Figure 1:
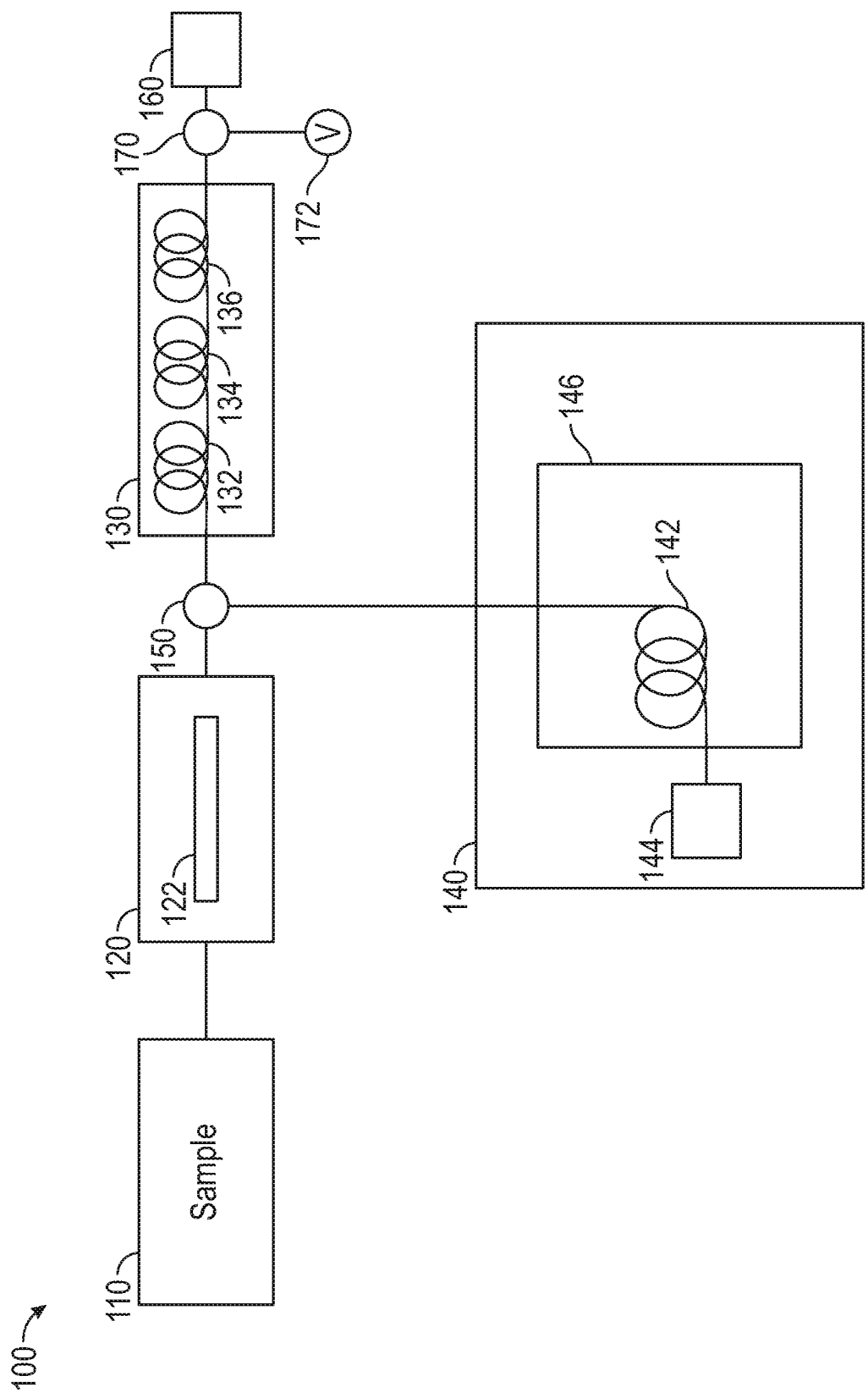
FIG. 1 illustrates an exemplary sample enrichment system according to some embodiments of the disclosure.

In the following description, reference is made to the accompanying drawings which form a part hereof, and in which it is shown by way of illustration specific examples that can be practiced. It is to be understood that other examples can be used and structural changes can be made without departing from the scope of the examples of the disclosure.

The disclosed system uses cold trap dehydration to eliminate water vapor in a first stage trap, but instead of a cold packed trap in the second stage it uses a sub-ambient temperature multi-capillary column trapping system (MCCTS) to concentrate the volatile chemicals. Using the MCCTS for trapping and focusing the sample eliminates the four major problems with packed traps, as described above.

First, the capillary traps have a smaller internal volume with better laminar flow and faster release rates upon thermal desorption than packed traps do so a subsequent liquid nitrogen (or electronically cooled) focusing trap is not necessary for sample enrichment and concentration. Direct, split-less injection can be made to the GC without further focusing after trapping with the cold MCCTS, saving time, the cost of liquid nitrogen, and simplifying the system in general.

The second problem is also eliminated because the particle size found in capillary columns have typical volumes that are 1000× smaller than those found in packed traps. This is possible with capillary columns without an increase in pressure drop because the particles only coat the walls of the capillary columns, leaving most of the inner diameter of the columns open to allow reasonable flow rates with little pressure drop. After desorbing a sample to a GC or GCMS, these smaller adsorbent particles can release residual chemicals hundreds of times faster during a system bake out, allowing much better system blank levels in a shorter period of time. This greatly improves system performance without shortening run times, while eliminating the down-time experienced when packed trap based systems are accidently exposed to high concentration samples that may require 1-2 days of system bake out prior to reestablishing acceptable blank levels.

The small particle size also eliminates the third problem by allowing the effective release of Carbon Dioxide and Nitrogen prior to any loss of C2 Hydrocarbons, simply due to the statistical probability of having N2 and CO2 purge out of particles faster that have only $\frac{1}{1000}^{th}$ the internal volume of typical packed trap adsorbent particles. This provides for better chromatography and reduces or eliminates background interferences common with many GC detectors for improved detection limits.

Finally, the MCCTS includes "open tubular" columns that have a wall coating of sorbent. The cross section of the open part of the open tubular columns is much greater than that of the coating. Therefore, the channeling and trapping of the compounds further into a packed trap due to expansion and contraction of the adsorbent do not occur when using an open tubular trap, as the open inner diameter of the trap remains about the same whether the trap is hot or cold. This improves the precision of these trapping systems, allowing them to achieve the level of reproducibility that is seen with loop injection or syringe injection that can approach +/−1% to 2%.

Using the MCCTS at reduced temperatures dramatically increases the adsorption affinity of chemicals to the capillary traps. It has been found that by reducing the temperature approximately 35° C., the traps display an increased adsorption strength of about 10×. Therefore, at −10° C., the traps can retain chemicals that will not be well retained at ambient temperatures (e.g. 25 to 35° C.), such as C2 Hydrocarbons and Formaldehyde, along with other light compounds. Making the trap even colder, say −40° C., can either make the trap much stronger, or can allow much shorter column segments than would be necessary at −10° C. The shorter the column segments that the chemicals can be deposited and retained on, the faster they will inject into a GC or GCMS. Also, the less adsorbent that is used (e.g. shorter column lengths), the faster the system will clean up after exposure to high concentration samples.

FIG. 1 illustrates an exemplary sample enrichment system 100 according to some embodiments of the disclosure. A gas phase sample 110 containing volatile chemicals is drawn or pushed through two traps 120 and 130 connected in series. In some embodiments, the system 100 includes the sample 110, the first trap 120, the second trap 130, chemical analyzer 140, flow controller and volume measurement system 160, and valve 172. The first trap 120 can include a section of tubing 122. The second trap 130 can include a first capillary column 132, a second capillary column 134, and a third capillary column 136 connected in series. The first trap 120 and second trap 130 can each include a heater, allowing the two traps to be heated independently from one another. Each trap 120 and 130 can further be thermally coupled to a respective cooling system, such as a liquid nitrogen cryogenic cooling system or an electronic cooling system and can therefore be cooled independently from one another. The system 100 can further include one or more processors (e.g., controllers, microprocessors, computers, computer systems, etc.) (not shown) running software and/or instructions housed on a non-transitory computer-readable medium for controlling the operation of one or more components of the system 100.

In some embodiments, the first trap 120 includes an open tube or column 120 that has an inert internal surface that will not adsorb or absorb volatile chemicals at the temperature it is being operated at. The tube 122 must have a large enough volume so that the collected water will not block the flow path, while being narrow enough to maintain a sufficient linear velocity and minimum surface area inside of the tube 122. In some embodiments, the tube 122 has an internal diameter between 0.03" and 0.1", a length between 1 and 12 inches, and a volume between 20-50 microliters, although other internal diameters, lengths, and volumes can also be used in some cases. The first trap 120 can further include a heater and can be cooled by a sub ambient cooling system, such as a liquid nitrogen cooling system, Freon-based cooling, a sterling engine, liquid CO2, or an electronic cooling system, such as a Peltier cooler. During sample trapping, the first trap 120 decreases the dew point of the sample 110 to a level in the range of −40° C. to −10° C. so that 95% to 99% of the water vapor can be separated from the rest of the sample, which can proceed to the second trap 130 of the system 100. This means of water elimination is effective because only water is typically in air or headspace samples within a factor of 1.1 to 10 of its saturation point in many situations. Most other compounds in the sample can be thousands of times below their saturation concentrations, and therefore they can be cooled substantially while still remaining in the gas phase. In addition, as water goes directly from the gas phase to the solid phase, even very water soluble compounds such as Formaldehyde and H2S can pass through the trap without losses because although these compounds are very soluble in liquid water, these compounds do not likewise interact with solid phase water so they are not retained by the first trap 120. As long as 95-99% of the water vapor is eliminated from the sample prior to analysis, a total sample volume of up to 1000 cc can be collected without significant effects to a capillary gas chromatograph or its detectors, including mass spectrometers.

The sample can flow from the first trap 120 directly to the second trap 130, through an intermediate switch valve, rotary valve, or pressure controlled "tee" connection 150. In some embodiments, the connection 150 enables back-flushing of the second trap 130 directly to a chemical analyzer 140 (e.g., a GC or GCMS) without passing back through the first trap 120. In some embodiments, the backflushing flow is facilitated by opening valve 172 to access a clean, contamination-free purge gas at 5-40 psig pressure. The second trap 130 can include 2-4 capillary columns, such as columns 132, 134, and 136, of increasing strength connected to each other in series. For example, the first capillary column 132 can be the weakest column and the third capillary column 136 can be the strongest column, with the second capillary column 134 having an intermediate strength relative to the other columns. In other words, the third capillary column 136 has a higher chemical affinity for one or more compounds of the sample than the second capillary column 134 or the first capillary column 132. The columns 132, 134, and 136 can absorb/adsorb all compounds of interest with boiling points from about −100° C. to >230° C. This range of boiling points encompasses a range of compounds from C2 Hydrocarbons to C12 Hydrocarbons, and which is the range of what the US EPA calls NMOCs, or Non-Methane Organic Compounds. They also refer to these as VOCs, or Volatile Organic Compounds. In some embodiments, heavier sample compounds can be trapped by the first capillary column 132, which can have the lowest strength, while lighter sample compounds can pass through the first capillary column 132 to be trapped by the second capillary column 134 or the third capillary column 136. In some embodiments, the flow rate of gas during trapping is in the range of 5-100 cc/min (e.g., 10-30 cc/min).

The columns 132, 134, and 136 are optionally placed in a heating mandrel or oven (not shown) so they can be cooled during trapping, and then heated during back-desorption into the chemical analyzer. In some embodiments, during trapping, the second trap 130 is cooled by a sub ambient cooling system, such as a liquid nitrogen cooling system, Freon-based cooling, a sterling engine, liquid CO2, or an electronic cooling system, such as a Peltier cooler. In some embodiments, the lengths of the columns range from just a few inches for each segment to a few meters. For example, the first column 132 can be a PDMS column with a length of 0.3-1 meters, the second column 134 can be a PLOT Q column with a length of 0.3-0.8 meters, and the third column 136 can be a PLOT Carboxen column with a length of 0.1-0.5 meters, though in some embodiments, the third column 136 may be longer to increase the trapping volume to greater than 500 cc when analyzing C2 Hydrocarbons. In some embodiments, each column is three to thirty times stronger than the column proceeding it (e.g., the second column 134 is three to thirty times stronger than the first column 132 and so on). Generally upon cooling to −20° C. to −50° C., the second trap 130 becomes roughly one hundred times stronger than when operating at +35° C., such as when using simple fan cooling. Thus, in some embodiments, the column 132, 134, and 136 lengths can be shorter compared to similar trapping systems that operate at higher temperatures (e.g., above 0° C., above 20° C., above 35° C., etc.) while still retaining all target VOCs.

After measuring the collected volume using a downstream volume measurement technique (such as using flow controller and volume measurement system 160, which can be a mass flow controller, fixed restrictor and fixed pressure over a given time period, or obtaining a desired pressure change in a known volume reservoir), the first trap 120 can be heated (e.g., using the heater of the first trap 120) to a temperature in the range of 0° C. to +20° C. to allow an additional, small volume (e.g., 5-40 cc) of carrier fluid (e.g., inert or non-reactive gas) to recover any VOCs of interest that had temporarily adsorbed within the first trap 120. The flow of this carrier fluid can be controlled by the flow controller and volume measurement system 160. Using a very small volume of carrier fluid will not significantly increase the amount of water vapor in the second trap 130, and can create a more complete recovery of some VOCs.

Then, the second trap 130 can be heated under no flow conditions to an elevated temperature (e.g., 100-250° C.) to allow faster release of the collected compounds into the chemical analyzer. After preheating, the carrier fluid is diverted into the second trap 130 to "back-flush" the trapped compounds into the chemical analyzer 140. During backflushing, flow can be introduced from the third column 136 to the first column 132, through connection 150 and into chemical analyzer 140. In some embodiments, when transferring one or more sample compounds from the second trap 130 to the chemical analyzer 140. The pressure controller facilitates the flow by controlling the pressure in the chemical separation column 142 based on the temperature of the oven 156 included in the chemical analyzer 140, the carrier fluid type (e.g., helium or hydrogen), the length and diameter of the chemical separation column 142, and the characteristics of one or more restrictors of the chemical analyzer 140, such as a restrictor at the inlet of chemical separation column 142 between connection 150 and chemical separation column 142. A quick ramping of the carrier gas pressure during injection can compress the chemicals to provide even a faster injection rate to create narrower on-column peak widths to improve sensitivity and resolution of one chemical peak from the next.

In some embodiments, the second trap 130 is heated during preheat with a thermal gradient by constructing the heater to heat the back (e.g., the stronger columns, such as the third column 136) of the trap 130 faster than the front of the trap (e.g., the weaker columns, such as the first column 132), which can also increase the injection rate. Such a thermal gradient works on this second trap 130 that includes multiple capillary columns far better than the effect of a thermal gradient on packed traps, because packed traps normally only contain 1-5" of bed length, whereas the combined length of 2 to 4 columns of the second trap can be 10-100", offering a longer path length for obtaining compression during thermal gradient desorption. Also, a fast temperature gradient cannot consistently heat up the entire packed trap radially as the adsorbent inside of the trap does not transmit heat to the center-line of the tube as fast as it transmits heat long the tube itself. For open tubular columns, the adsorbents or polymeric coatings are only on the inner walls of the tubing, and almost instantly take on the temperature of the tubing that they are coated onto. The smaller particles sizes used in the capillary columns of the second trap 130 can allow faster release and higher resolution chromatography than prior packed trap technology.

After transferring the sample from the second trap 130 to the chemical separation column 142, the first trap 120 and second trap 130 can be baked out and backflushed to remove excess water (e.g., from the first trap 120) and any residual sample compounds remaining in the first trap 120 or the second trap 130. During backflushing, a flow is introduced by opening valve 172 to release a flow of carrier fluid through the first trap 120 and the second trap 130 in the reverse direction (e.g., from the second trap 130 to the first trap 120). Valve 172 can include a sintered stainless steel frit or critical orifice restrictor to limit the backflush flow to 5-100 cc/min when using a pressure of 5-40 psig of clean gas released through the valve 172, for example. The temperature of the first column 120 and second column 130 can be in the range of 100-300° C. during bake out.

Figure 2:
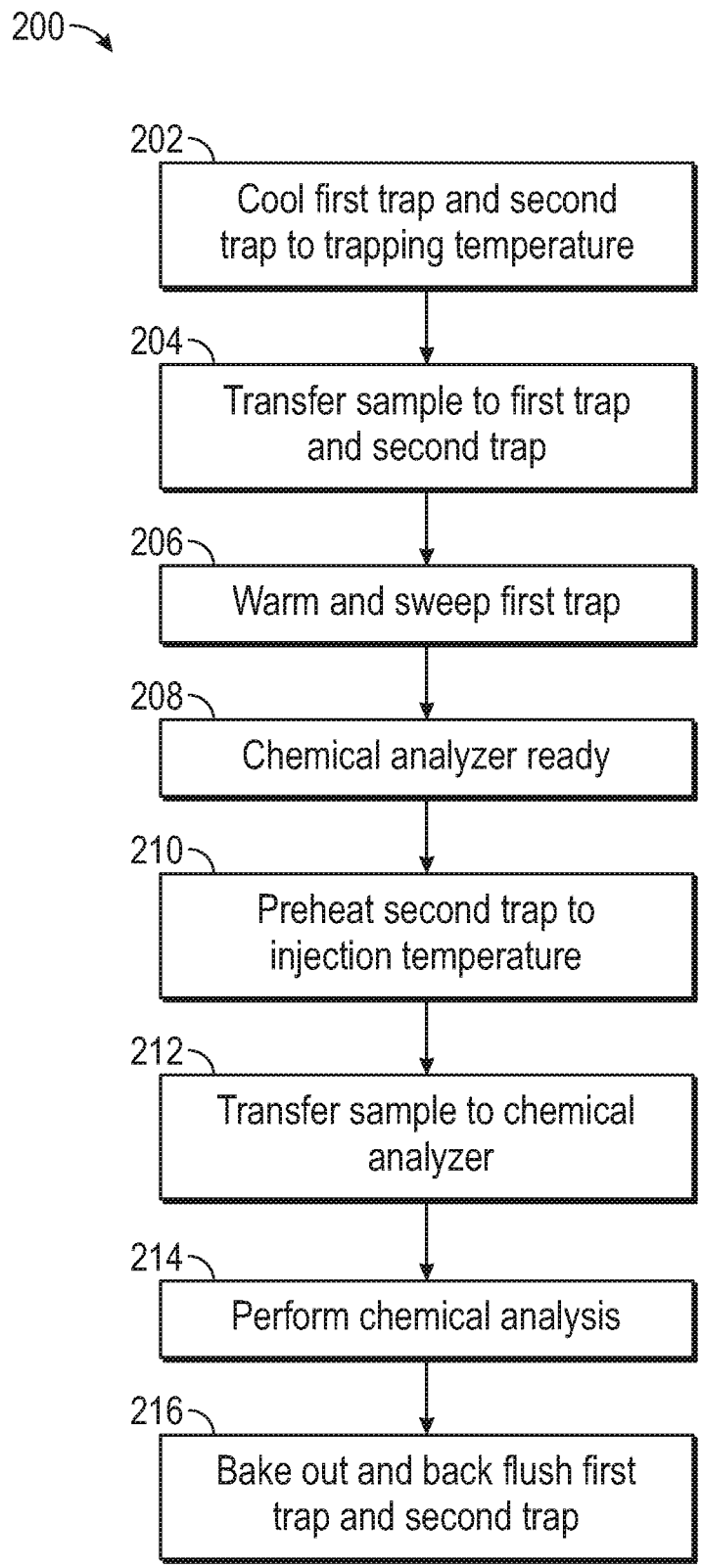
FIG. 2 illustrates an exemplary process according to some embodiments of the disclosure.

FIG. 2 illustrates an exemplary process 200 according to some embodiments of the disclosure. Process 200 can be performed using system 100 described above with reference to FIG. 1. In some embodiments, one or more processors (e.g., controllers, microprocessors, computers, computer systems, etc.) (not shown) running software and/or instructions housed on a non-transitory computer-readable medium can control the operation of one or more components of the system 100 to perform process 200.

In step 202, the first trap 120 and second trap 130 are cooled to the trapping temperature using either electronic cooling, Freon-based cooling, a sterling engine, liquid nitrogen, or liquid CO2. In some embodiments, the trapping temperature is in the range of 0 to −60° C. for each trap, such as −40° C. The first trap 120 and second trap 130 can be cooled to the same trapping temperature or to different trapping temperatures.

In step 204, the sample is transferred to the first trap 120 and the second trap 130 with unretained fixed gasses going to the flow controller and volume measurement system 160. While introducing the sample in this way, the flow controller and volume measurement system 160 can measure the volume of gas transferred through the traps 120 and 130. The transferred gas can be an internal standard gas, a calibration gas, or the sample to be measured, or any or all of these one after the other in any combination, such as to support internal standard or external standard GC methods, and to support matrix spiking of the target compounds during a sample analysis. In some embodiments, the flow rate of gas during trapping is in the range of 5-100 cc/min (e.g., 10-30 cc/min).

While the sample is transferred to the first trap 120 and the second trap 130 in step 204, excess moisture can be removed from the sample, the internal standard, the calibration standard, or a humidified blank gas at the first trap 120. The amount of removal can be determined by the temperature and therefore the dew point of the gas exiting the first trap 120. For example, if the first trap 120 has a temperature of −40° C., compounds boiling at −100° C. to +230° C. should not condense out at concentrations of lPPM and below because they can still be above their respective saturation points.

While the sample is transferred to the first trap 120 and second trap 130, compounds boiling from −100° C. to +230° C. can be quantitatively trapped and retained on the second trap 130 at temperatures from 0 to −50° C.

In step 206, in some embodiments, the first trap 120 is "swept" to transfer remaining target compounds to the second trap 130 with minimal transfer of water vapor from the first trap 120 to the second trap 130. After the volume of each gas is collected (sample, internal standard, calibration standard, blank gas), the first trap 120 can be heated to a slightly warmer temperature, such as from 0° C. to +20° C., or in some embodiments, 10° C., which can keep water vapor concentrations reasonably low, to allow a very small additional volume of an inert gas such as helium or nitrogen to pass through the first trap 120 to the second trap 130 to "sweep" any compounds that adsorbed temporarily onto the first trap 120 while at the colder trapping temperature. In some embodiments, a small amount of gas (e.g., 5-40 cc) will not deliver a significant amount of the condensed water to the second trap 130, but can increase the recovery of some compounds. The flow of gas for sweeping the first trap 120 can be controlled by the flow controller and volume measurement system 160. In some embodiments, the flow rate of the "sweep" gas is in the range of 5-100 cc/min (e.g., 5-20 cc/min).

In step 208, the chemical analyzer 140 generates a READY signal, indicating it is ready to receive a sample for chemical separation and detection. When the analyzer 140 is ready for the next injection, the second trap 130 can be pre-heated in step 210 to an elevated temperature (e.g., 100-250° C.). After preheating, the carrier gas (e.g., Helium or Hydrogen gas) can be diverted to back flush the trapped compounds from the second trap 130 to the chemical analyzer 140 in step 212, and the analysis commences in step 214. The flow of gas from the second trap 130 to the chemical analyzer 140 can be controlled by a pressure controller of the chemical analyzer 140, as described above. In some embodiments, the flow rate of gas during the transfer of the sample from the second trap 130 to the chemical analyzer 140 is in the range of 0.3-3 cc/min. The flow rate optionally increases over time, with an initial flow rate in the range of 0.3-1 cc/min that increases to 1-3 cc/min after injection has started. As described previously, a rapid rise in carrier fluid pressure and/or the use of a thermal gradient that heats the back of the second trap 130 sooner than the front can both provide a faster injection rate into the chemical analyzer 140. The faster the injection rate, the narrower the compounds are on the chemical separation column 142, and the easier it will be to "resolve" or separate them from one another. Narrow peak widths may also result in "taller" peaks, thereby improving the signal to noise ratio providing better detection limits, which is critical for trace level analysis. During the chemical analysis, the gas including the sample compounds and a carrier gas (e.g., Hydrogen or Helium) moves through the chemical separation column 142 at a flow rate of 0.3-3 cc/min.

After injection, in step 216, the first trap 120 and the second trap 130 are briefly baked out in the "back-flushed" direction (e.g., from the second trap 130 to the first trap 120), and then are cooled down to process the next sample. The back-flush flow of gas through the second trap 130 and the first trap 120 in the reverse direction (e.g., from the second trap 130 to the first trap 120) can be controlled by valve 172 with its associated frit or critical orifice to limit the flow rates to between 5-100 cc/min (e.g., 20-30 cc/min). A carrier fluid such as ultra-high purity Nitrogen or Helium can be used during back-flushing.

The system 100 can be used for improving or optimizing trace level analysis of VOCs and similar chemicals in a gas phase sample. The "headspace" above a liquid or solid sample can also be analyzed by allowing the headspace to achieve equilibrium with the liquid or solid in a closed system followed by transferring the headspace gas into the trapping system. Cylinder gases can be tested for impurities, such as hydrogen sulfide and other sulfur species in carbon dioxide used to make carbonated beverages. Process streams in refineries can be tested for trace level impurities, either online or by using collection containers or bags. Low detection limits can be obtained during analysis of aromas, flavors, fragrances, and off-odor compounds when characterizing foods, beverages, and all consumer products.

One very important use of this invention is for the improved analysis of Environmentally collected samples of outdoor air, indoor air, soil gas, landfill gas, and stack gas for toxic chemicals and chemicals that are known to increase ozone production in urban air. These samples can either be introduced directly into the preconcentration system and GC or GCMS, or samples can be collected in Tedlar bags, or using vacuum sampling canisters as described in US EPA Method TO15, Chinese Method HJ759-2015, and others. The lower blank levels offered by the small particles in the second trap 130 that includes multiple capillary columns 132, 134, and 136 connected in series compared to classical packed traps is the result of their ability to clean up much faster and to lower levels of contamination, resulting in lower detection limits using today's high sensitivity mass spectrometers. Ultimate detection limits of these introduction systems are generally limited by how clean they are; that is, their chemical background level. By decreasing "chemical noise", a system can immediately achieve a greater "signal to noise ratio", which is ultimately what determines detection limits of any chemical analyzer.

Therefore, according to the above, in some embodiments, a system comprises a first trap comprising a first tube; a second trap, the second trap comprising multiple capillary columns coupled in series, the second trap situated inside a second heater, the second heater configured to: during a second time period, heat the second trap to a desorption temperature; a chemical analyzer including a pressure controller; one or more cooling systems configured to: during a first time period prior to the second time period, cool the first trap and the second trap to a trapping temperature; and a flow controller configured to during the first time period, control a flow and flow volume of carrier gas in a first direction that transfers one or more compounds of a chemical sample to the first trap and the second trap, and transfers a portion of water of the chemical sample to the first trap without transferring the portion of water to the second trap, wherein: the pressure controller of the chemical analyzer is configured to, during the second time period, facilitate a flow of carrier gas in a second direction opposite the first direction that transfers the one or more compounds of the chemical sample from the second trap to the chemical analyzer without transferring the portion of water from the first trap to the chemical analyzer. Additionally or alternatively, in some embodiments the portion of water of the chemical sample is removed from the first trap after the one or more compounds of the sample are transferred from second trap to the chemical analyzer. Additionally or alternatively, in some embodiments the flow controller is further configured to, after transferring the one or more compounds of the chemical sample to the second trap and before transferring the one or more compounds of the chemical sample from the second trap to the chemical analyzer, control a sweep flow of carrier gas in the first direction to transfer one or more compounds of the sample from the first trap to the second trap without transferring the portion of the water from the first trap to the second trap. Additionally or alternatively, in some embodiments the system further comprises a first heater, wherein the first trap is situated in the first heater, and the first heater is configured to, while the flow controller controls the sweep flow in the first direction, heat the first trap to a sweep temperature that is greater than the trapping temperature and low enough to retain the portion of water in the first trap. Additionally or alternatively, in some embodiments the multiple capillary columns of the second trap comprise a first capillary column having a first strength and a second capillary column having a second strength greater than the first strength, the first capillary column between the first trap and the second capillary column. Additionally or alternatively, in some embodiments the trapping temperature is in the range of −60 degrees Celsius to 0 degrees Celsius and the desorption temperature is in the range of 100 degrees Celsius to 250 degrees Celsius. Additionally or alternatively, in some embodiments the chemical analyzer comprises a gas chromatograph or a gas chromatograph-mass spectrometer. Additionally or alternatively, in some embodiments the system further comprises a valve and flow restrictor fluidly coupled to the second trap; a first heater wherein: the first trap is situated in the first heater, the first heater and the second heater are further configured to heat the first trap and the second trap to a bake out temperature greater than the trapping temperature during a third time period after the second time period, and the valve and flow restrictor are configured to control a flow in the second direction through the second trap and the first trap during the third time period. Additionally or alternatively, in some embodiments the one or more cooling systems comprise one or more of an electronic cooling system, a Freon-based cooling system, a liquid carbon dioxide cooling system or a liquid nitrogen cooling system.

Additionally or alternatively, in some embodiments, a method comprises cooling, with one or more cooling systems, a first trap and a second trap to a trapping temperature, the first trap comprising a first tube and the second trap comprising multiple capillary columns coupled in series and situated in a second heater, transferring one or more compounds of a chemical sample to the first trap and the second trap while the first trap and second trap are at the trapping temperature, wherein: the chemical sample includes a portion of water that remains in the first trap without being transferred to the second trap while the one or more compounds of the chemical sample are transferred to the second trap, and transferring the one or more compounds of the chemical sample to the first trap and the second trap comprises controlling a flow, with a flow controller, in a first direction; heating, with the second heater, the second trap to a desorption temperature; and transferring the one or more compounds of the chemical sample from the second trap to a chemical analyzer, wherein transferring the one or more compounds of the chemical sample from the second trap to the chemical analyzer comprises facilitating a flow, with a pressure controller of the chemical analyzer, in a second direction opposite from the first direction without transferring the portion of water from the first trap to the chemical analyzer. Additionally or alternatively, in some embodiments the method further comprises removing the portion of water of the chemical sample from the first trap after the one or more compounds of the sample are transferred from second trap to the chemical analyzer. Additionally or alternatively, in some embodiments the method further comprises after transferring the one or more compounds of the chemical sample to the second trap and before transferring the one or more compounds of the chemical sample from the second trap to the chemical analyzer, controlling, with the flow controller, a sweep flow in the first direction to transfer one or more compounds of the sample from the first trap to the second trap without transferring the portion of the water from the first trap to the second trap. Additionally or alternatively, in some embodiments the method further comprises while the flow controller controls the sweep flow in the first direction, heat, with a first heater, the first trap to a sweep temperature that is greater than the trapping temperature and low enough to retain the portion of water in the first trap, wherein the first trap is situated in the first heater. Additionally or alternatively, in some embodiments the multiple capillary columns of the second trap comprise a first capillary column having a first strength and a second capillary column having a second strength greater than the first strength, the first capillary column between the first trap and the second capillary column. Additionally or alternatively, in some embodiments the trapping temperature is in the range of −60 degrees Celsius to 0 degrees Celsius and the desorption temperature is in the range of 100 degrees Celsius to 250 degrees Celsius. Additionally or alternatively, in some embodiments the chemical analyzer comprises a gas chromatograph or a gas chromatograph-mass spectrometer. Additionally or alternatively, in some embodiments the method further comprises during a third time period after the second time period: heating, with a first heater, the first trap to a bake out temperature greater than the trapping temperature, wherein the first trap is situated in the first heater, heating, with the second heater, the second trap to the bake out temperature; and controlling, a valve and flow restrictor that are fluidly coupled to the second trap, a flow in the second direction through the second trap and the first trap. Additionally or alternatively, in some embodiments the one or more cooling systems comprise one or more of an electronic cooling system, a Freon-based cooling system, a liquid carbon dioxide cooling system or a liquid nitrogen cooling system.

Although examples have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:
1. A system comprising:
a first trap comprising a first tube;
a second trap, the second trap comprising a first capillary column and a second capillary column coupled in series, the second trap situated inside a heater;
a chemical analyzer including a pressure controller;
one or more cooling systems configured to:
during a first time period, cool the first trap and the second trap to a trapping temperature, wherein cooling the first trap to the trapping temperature causes water of a chemical sample to transition directly from a gas phase to a solid phase and allows one or more water soluble compounds of the chemical sample to traverse the first trap; and
a flow controller configured to, during the first time period, control a flow and flow volume of carrier gas in a first direction that transfers one or more compounds of the chemical sample to the first trap and the second trap, including transferring the one or more compounds of the chemical sample from the first capillary column of the second trap to the second capillary column of the second trap, and transfers a portion of the water of the chemical sample to the first trap without transferring the portion of water to the second trap, wherein:
the pressure controller of the chemical analyzer is configured to, during a second time period after the first time period, facilitate a flow of carrier gas in a second direction opposite the first direction that transfers the one or more compounds of the chemical sample from the second trap to the chemical analyzer, including transferring the one or more compounds of the chemical sample from the second capillary column of the second trap to the chemical analyzer through the first capillary column of the second trap, without transferring the portion of water from the first trap to the chemical analyzer, wherein the heater is configured to:
during the second time period, heat the second trap to a desorption temperature.

2. The system of claim 1, wherein the portion of water of the chemical sample is removed from the first trap after the one or more compounds of the sample are transferred from second trap to the chemical analyzer.

3. The system of claim 1, wherein the flow controller is further configured to, after transferring the one or more compounds of the chemical sample to the second trap and before transferring the one or more compounds of the chemical sample from the second trap to the chemical analyzer, control a sweep flow of carrier gas in the first direction to transfer one or more compounds of the sample from the first trap to the second trap without transferring the portion of the water from the first trap to the second trap.

4. The system of claim 3, further comprising:
a first heater, wherein the first trap is situated in the first heater, and the first heater is configured to, while the flow controller controls the sweep flow in the first direction, heat the first trap to a sweep temperature that is greater than the trapping temperature and low enough to retain the portion of water in the first trap.

5. The system of claim 1, wherein the trapping temperature is in the range of −60 degrees Celsius to 0 degrees Celsius and the desorption temperature is in the range of 100 degrees Celsius to 250 degrees Celsius.

6. The system of claim 1, wherein the chemical analyzer comprises a gas chromatograph or a gas chromatograph-mass spectrometer.

7. The system of claim 1 further comprising:
a valve and flow restrictor fluidly coupled to the second trap;
a first heater wherein:
the first trap is situated in the first heater,
the first heater and the heater are further configured to heat the first trap and the second trap to a bake out temperature greater than the trapping temperature during a third time period after the second time period, and
the valve and flow restrictor are configured to control a flow in the second direction through the second trap and the first trap during the third time period.

8. The system of claim 1, wherein the one or more cooling systems comprise one or more of an electronic cooling system, a Freon-based cooling system, a liquid carbon dioxide cooling system or a liquid nitrogen cooling system.

9. A method comprising:
during a first time period, cooling, with one or more cooling systems, a first trap and a second trap to a trapping temperature, the first trap comprising a first tube and the second trap comprising a first capillary column and a second capillary column coupled in series and situated in a heater, wherein cooling the first trap to the trapping temperature causes water of a chemical sample to transition directly from a gas phase to a solid phase and allows one or more water soluble compounds of the chemical sample to traverse the first trap;
transferring one or more compounds of the chemical sample to the first trap and the second trap, including transferring the one or more compounds of the chemical sample from the first capillary column of the second trap to the second capillary column of the second trap, while the first trap and second trap are at the trapping temperature, wherein:
the chemical sample includes a portion of water that remains in the first trap without being transferred to the second trap while the one or more compounds of the chemical sample are transferred to the second trap, and
transferring the one or more compounds of the chemical sample to the first trap and the second trap comprises controlling a flow, with a flow controller, in a first direction;
during a second time period after the first time period, heating, with the second heater, the second trap to a desorption temperature; and
transferring the one or more compounds of the chemical sample from the second trap to a chemical analyzer, including transferring the one or more compounds of the chemical sample from the second capillary column of the second trap to the chemical analyzer through the first capillary column of the second trap, wherein transferring the one or more compounds of the chemical sample from the second trap to the chemical analyzer comprises facilitating a flow, with a pressure controller of the chemical analyzer, in a second direction opposite from the first direction without transferring the portion of water from the first trap to the chemical analyzer.

10. The method of claim 9, further comprising:
removing the portion of water of the chemical sample from the first trap after the one or more compounds of the sample are transferred from second trap to the chemical analyzer.

11. The method of claim 9, further comprising:
after transferring the one or more compounds of the chemical sample to the second trap and before transferring the one or more compounds of the chemical sample from the second trap to the chemical analyzer, controlling, with the flow controller, a sweep flow in the first direction to transfer one or more compounds of the sample from the first trap to the second trap without transferring the portion of the water from the first trap to the second trap.

12. The method of claim 11, further comprising:
while the flow controller controls the sweep flow in the first direction, heat, with a first heater, the first trap to a sweep temperature that is greater than the trapping temperature and low enough to retain the portion of water in the first trap, wherein the first trap is situated in the first heater.

13. The method of claim 9, wherein the trapping temperature is in the range of −60 degrees Celsius to 0 degrees Celsius and the desorption temperature is in the range of 100 degrees Celsius to 250 degrees Celsius.

14. The method of claim 9, wherein the chemical analyzer comprises a gas chromatograph or a gas chromatograph-mass spectrometer.

15. The method of claim 9, further comprising:
during a third time period after the second time period:
heating, with a first heater, the first trap to a bake out temperature greater than the trapping temperature, wherein the first trap is situated in the first heater;
heating, with the heater, the second trap to the bake out temperature; and controlling, a valve and flow restrictor that are fluidly coupled to the second trap, a flow in the second direction through the second trap and the first trap.

16. The method of claim 9, wherein the one or more cooling systems comprise one or more of an electronic cooling system, a Freon-based cooling system, a liquid carbon dioxide cooling system or a liquid nitrogen cooling system.

\* \* \* \* \*

UNITED STATES PATENT AND TRADEMARK OFFICE
CERTIFICATE OF CORRECTION

| | |
|---|---|
| PATENT NO. | : 11,162,925 B2 |
| APPLICATION NO. | : 16/175230 |
| DATED | : November 2, 2021 |
| INVENTOR(S) | : Daniel B. Cardin |

It is certified that error appears in the above-identified patent and that said Letters Patent is hereby corrected as shown below:

In the Claims

In Column 13, Line 13, in Claim 2, please delete "the sample" and insert --the chemical sample--

In Column 13, Line 21, in Claim 3, please delete "the sample" and insert --the chemical sample--

In Column 13, Line 32, in Claim 5, please delete "the range" and insert --a range--

In Column 13, Line 33, in Claim 5, please delete "the range" and insert --a range--

In Column 14, Line 16, in Claim 9, please delete "the second heater" and insert --the heater--

In Column 14, Line 34, in Claim 10, please delete "the sample" and insert --the chemical sample--

In Column 14, Line 43, in Claim 11, please delete "the sample" and insert --the chemical sample--

In Column 14, Line 54, in Claim 13, please delete "the range" and insert --a range--

In Column 14, Line 55, in Claim 13, please delete "the range" and insert --a range--

Signed and Sealed this
Twenty-third Day of January, 2024

Katherine Kelly Vidal
*Director of the United States Patent and Trademark Office*